United States Patent
Cupp et al.

(10) Patent No.: US 6,219,565 B1
(45) Date of Patent: Apr. 17, 2001

(54) METHODS AND APPARATUS FOR NON-INVASIVE GLUCOSE SENSING: NON-INVASIVE PROBE

(75) Inventors: James Cupp; Raymond Fowler, both of Indiana, PA (US)

(73) Assignee: Diasense, Inc., Pittsburgh, PA (US)

( * ) Notice: Subject to any disclaimer, the term of this patent is extended or adjusted under 35 U.S.C. 154(b) by 0 days.

(21) Appl. No.: 09/117,756
(22) PCT Filed: Feb. 5, 1997
(86) PCT No.: PCT/US97/01450
§ 371 Date: Dec. 3, 1998
§ 102(e) Date: Dec. 3, 1998
(87) PCT Pub. No.: WO97/27800
PCT Pub. Date: Aug. 7, 1997

Related U.S. Application Data

(60) Provisional application No. 60/011,193, filed on Feb. 5, 1996.

(51) Int. Cl.[7] ........................................................ A61B 5/00
(52) U.S. Cl. ............................................. 600/310; 600/316
(58) Field of Search ..................................... 600/310, 311, 600/316, 322, 323, 342, 473, 476; 356/39; 385/115

(56) References Cited

U.S. PATENT DOCUMENTS

| | | |
|---|---|---|
| 5,070,874 | 12/1991 | Barnes et al. . |
| 5,178,142 | 1/1993 | Harjunmaa et al. . |
| 5,419,321 | 5/1995 | Evans . |
| 5,460,177 | 10/1995 | Purdy et al. . |
| 5,551,422 * | 9/1996 | Simonsen et al. .................. 600/322 |
| 5,596,992 | 1/1997 | Haaland et al. . |
| 5,754,715 * | 5/1998 | Melling ................................ 385/115 |
| 5,803,909 * | 9/1998 | Maki et al. ........................... 600/310 |

* cited by examiner

Primary Examiner—Eric F. Winakur
(74) Attorney, Agent, or Firm—Webb Ziesenheim Logsdon Orkin & Hanson, P.C.

(57) ABSTRACT

Disclosed is a probe 2 suitable for use in the non-invasive sensing of glucose concentrations in the body of a patient. The probe 2 includes at least three radiation receiving fibers 16 extending between a probe body 12 and a spectrograph 8, and spaced apart from each other in a substantially uniform manner and aligned in a predetermined fixed pattern at the probe body 12. A radiation transmitting means 10 conducts radiation from a radiation source 4 and extends from the radiation source 4 to the probe body 12. The radiation transmitting means 10 is formed in the probe 2 into ring means for conducting radiation in a ring-shaped area immediately surrounding each of said receiving fibers 16. The radiation transmitting means 10 and the receiving fibers 16 terminate at the probe body 12 in a unitary structure having an outer surface configured for contacting the skin of a patient. The ring means passes radiation from the radiation source 4 into the patient in the areas immediately surrounding each receiving fiber 16. The receiving fibers 16 detect the radiation passing back out of the patient and pass this detected radiation to the spectrograph 8.

20 Claims, 4 Drawing Sheets

METHODS AND APPARATUS FOR NON-INVASIVE GLUCOSE SENSING: NON-INVASIVE PROBE

This application claims benefit of provisional application 60/011,193 filed Feb. 5, 1996. This application is a 371 of PCT/US97/01450 filed Feb. 5, 1997.

BACKGROUND OF THE INVENTION

1. Field of the Invention

This invention relates to the non-invasive sensing of blood glucose levels and, more particularly, to a non-invasive probe suitable for use with a non-invasive blood glucose monitor for patients with diabetes.

2. Description of the Prior Art

It is generally known in the art that radiation, particularly near-infrared radiation over a range of wavelengths, can be projected in a non-invasive manner on a portion of the body of a patient. The resulting radiation emitted from that portion of the body, either scattered or transmitted after absorption and scattering, can be detected and processed to derive an expression of the detected radiation as a function of wavelength and, therefrom, the concentration of blood glucose. Since the detected radiation is a continuous signal covering all of the wavelengths in the range of interest, it is necessary for further analysis to separate the intensities of radiation at the various individual wavelengths, or smaller bands of wavelengths, to extract the desired blood glucose level information.

U.S. Pat. Nos. 5,070,874 and 5,460,177 describe methods for the non-invasive measurement of blood glucose levels. In general, these methods use a spectrophotometer to measure the absorbance of the near-infrared radiation at different wavelengths across the range of interest. The absorbance plotted against the wavelengths constitutes a spectrum. By analyzing the spectrum, the blood glucose levels, or changes thereto, can be determined. As the blood glucose levels vary, the detected spectrum changes slightly.

In order to make the measurements discussed above, the radiation must be transmitted from a radiation source to the skin of a patient and the detected radiation received back from the patient must be collected and carried to the spectrophotometer for further analysis. Prior art fiber optic bundles are typically arranged in a completely coherent or ordered manner, in order to provide an image transfer capability, or are arranged in a completely incoherent or unordered manner and function as a simple light conduit for applications in which an imaging capability is unimportant. The much more expensive coherent fiber bundles are commonly used in medical and industrial probes, such as endoscopes and borescopes. Much less expensive incoherent fiber bundles are suitable for use in connection with non-imaging detectors and for specialized illuminators, such as those used in microscopy. Prior art fiber optic bundles that combine transmitting and receiving fibers are typically used some distance from their intended target and rely on reflection of the transmitted light by the target surface to illuminate the receiving fibers.

The prior art does not in any way address the high level of mechanical and thermal isolation of the return or receiving fibers necessary for the proper function of the fiber optic probe in glucose detection. Microbending stresses in the receiving fibers induced by various vibration sources from both within and outside the glucose monitor can produce intensity variations in the spectral signal being received from the patient and can thereby induce errors in the resulting spectral data. Thermal changes along the length of the receiving fibers, globally, localized or transient, have experimentally been shown to produce similar variations in the spectral signal, resulting in errors in the spectral data received from the patient.

SUMMARY OF THE INVENTION

In order to overcome the problems of the prior art discussed above, we have developed a cost-effective probe which combines the low-cost advantages of an incoherent fiber optic bundle for the transmitting fibers with the advantages of coherently arranged receiving fibers in the bundle. In contrast to the prior art, the present invention is designed to operate in intimate contact with its intended target, i.e., the human skin, and deliberately avoids direct surface reflections. In a preferred embodiment, the probe combines an incoherent transmissive fiber optic bundle with a small number of spaced receiving fibers arranged in a specialized, regular pattern to optimize received-signal intensity in a glucose measurement application. A preferred embodiment also includes uniquely designed features to thermally and/or mechanically isolate the receiving fibers extending from the probe in order to enhance their operation in a glucose measurement application.

DESCRIPTION OF THE PREFERRED EMBODIMENTS

Figure 1:
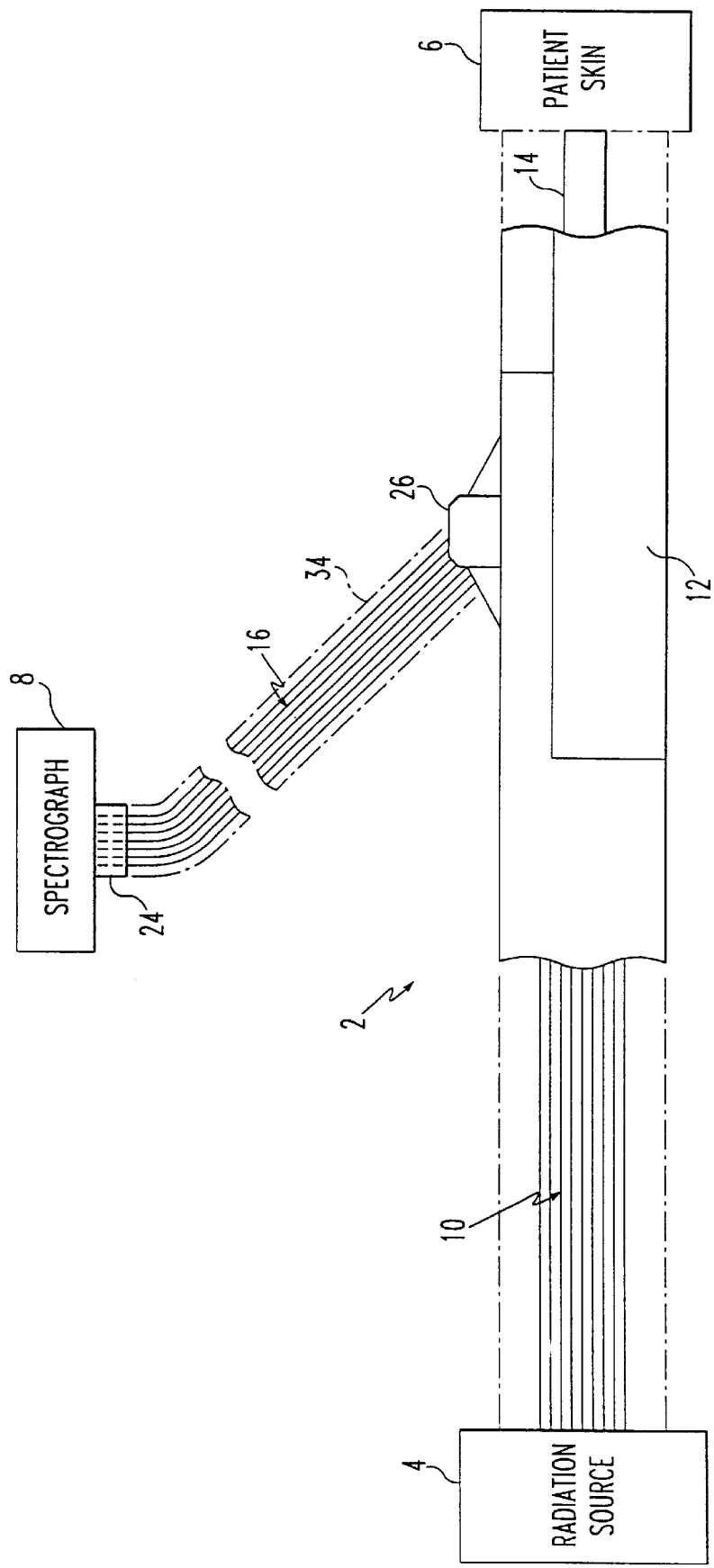
FIG. 1 is a schematic view of the elements of a probe in accordance with the present invention.

A probe 2 suitable for use in the non-invasive sensing of glucose concentrations in the body of a patient in accordance with the present invention is shown in FIGS. 1–5. As shown in more detail in FIG. 1, the present invention includes a bifurcated fiber optic bundle capable of transmitting radiation, particularly in the near-infrared range, and the fiber optic bundle has terminations at a radiation source 4, at the patient skin 6 and at a spectrograph 8. These terminations are shown in more detail in FIGS. 2, 3 and 4, respectively, and will be discussed hereinafter in more detail. With continued reference to FIG. 1, a plurality of transmitting fibers 10 in the form of a bundle extends from the radiation source 4 to a probe body 12 and terminates in a contact section 14 which comes in contact with the patient skin 6. A plurality of receiving fibers 16 extends from the spectrograph 8 and into the probe body 12 and terminates at the contact section 14. Most of the fibers are contained in a transmitting channel formed from the transmitting fibers 10, which carry spectrally filtered infrared radiation from the radiation source 4 to the skin interface at the contact section 14 in contact with the patient skin 6. A significantly smaller number of receiving fibers 16, interspersed in a regular pattern among the transmitting fibers 10 in the probe body 12 at the contact section 14, forms a receiving channel. One end of each of the receiving fibers 16 is in the contact section 14 in contact with the patient skin 6 while the other end of each of the receiving fibers 16 contacts the spectrograph 8 where the received radiation from the patient skin 6 exits the receiving fibers 16 and enters the spectrograph 8 for analysis.

Figure 2:
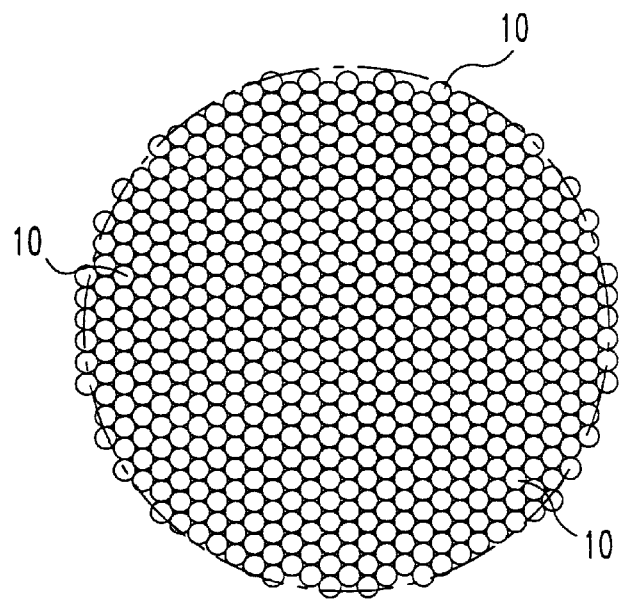
FIG. 2 is an end view of the transmitting fiber bundle extending from the radiation source.

As shown in FIG. 2, the transmitting fibers 10 at the radiation source 4 are arranged in an incoherent manner and, as shown, are hexagonally packed in a circular pattern for optimum density. The pattern shown in FIG. 2 is matched to the circularly symmetric shape of a known radiation source, having an illumination spot from a lamp reflector, in accordance with a preferred embodiment. However, other shapes matched to other radiation sources are possible and are included within the scope of the present invention. By describing the arrangement of the transmitting fibers 10 at the radiation source 4 as incoherent, it is meant that there is no particular prescribed location for any one of the transmitting fibers 10, rather the transmitting fibers 10 can be randomly arranged since they are all carrying the entire wavelength range of the radiation generated by the radiation source 4.

Figure 3:
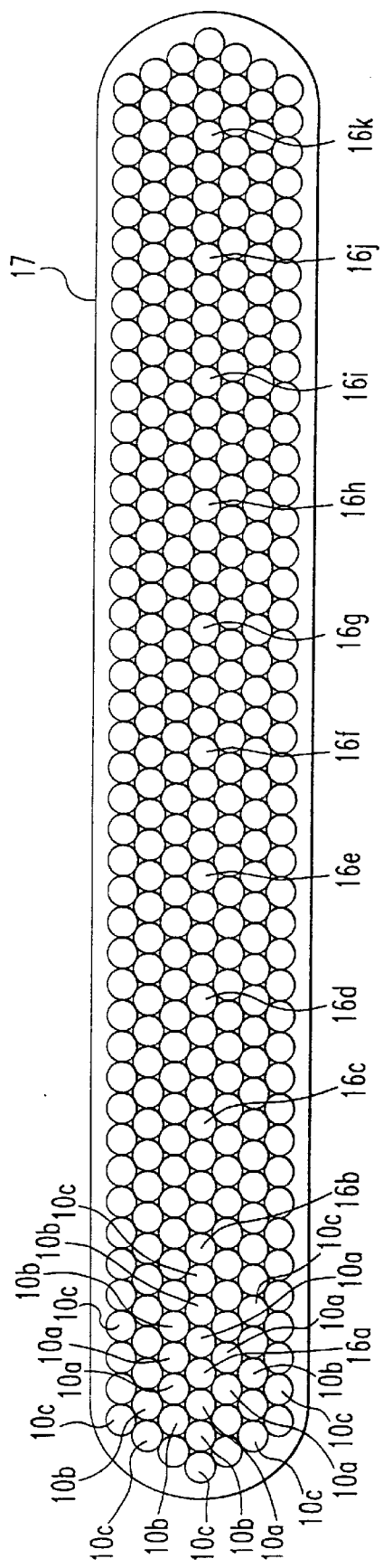
FIG. 3 is an end view of the transmitting fiber bundle and receiving fibers where they contact the skin of a patient.

As shown with reference to both FIGS. 1 and 3, the transmitting fibers 10 and the receiving fibers 16 join in the probe body 12, and the entire assembly is splayed out in a quasi-rectangular pattern at the contact section 14 or skin termination, where all fibers 10, 16 are connected in a unitary structure, such as by epoxy 17 or other adhesive, and preferably terminate in a common plane achieved by polishing or other means forming an outer surface configured for contacting the patient skin 6. Although a flat contact is presently preferred, other arrangements are possible. In a preferred embodiment, the fibers 10, 16 are arranged in seven hexagonally packed rows. Shown in FIG. 3 is a preferred embodiment including eleven receiving fibers 16a through 16k constrained to a central row, and each receiving fiber 16 is completely surrounded by transmitting fibers 10. In this arrangement, three transmitting fibers 10 in the central row are provided immediately on each side of each receiving fiber. All other rows shown in FIG. 3 contain only transmitting fibers. Therefore, it can be seen that each receiving fiber is at the center of three concentric hexagons or rings of transmitting fibers 10. For example, a first ring of transmitting fibers 10 surrounding receiving fiber 16a includes six transmitting fibers 10a. The twelve transmitting fibers 10b immediately contacting transmitting fibers 10a form a second ring surrounding receiving fiber 16a. The eighteen transmitting fibers 10c immediately contacting transmitting fibers 10b form a third ring surrounding receiving fiber 16a. Similar rings are formed around each of the ten other receiving fibers 16. It can be seen that certain transmitting fibers 10 form part of a ring around adjacent of the receiving fibers 16. For example, transmitting fiber 10a in the central row of fibers and immediately to the right of receiving fiber 16a as viewed in FIG. 3 is part of the first ring surrounding receiving fiber 16a and is part of a third ring surrounding receiving fiber 16b.

In a broader sense, all that is necessary for operation of the present invention is that the radiation receiving fibers 16 be spaced apart from each other and aligned in a predetermined fixed pattern, such as a substantially straight line, at the contact section 14 where they touch the patient skin 6. Radiation is then provided in a ring-shaped area immediately surrounding each receiving fiber 16. It is preferred that at least one ring-shaped area be provided around each receiving fiber 16, although multiple, nested rings, or one larger ring, can be provided around each receiving fiber 16. Although the means for transmitting radiation from the radiation source 4 to the patient skin 6 could be formed from other structures, such as individually formed radiation transmitting tubes, or a solid structure having bore holes therein for the receiving fibers 16, it is believed that the arrangement shown herein with a multiplicity of smaller transmitting fibers 10, which are readily available in the market, forming the means for transmitting the radiation from the radiation source 4 to the patient skin 6, provides an ideal construction method both in terms of expense and ease of construction. The transmitting fibers 10 at the contact section 14, other than arranged as shown in FIG. 3, are essentially arranged in an incoherent manner.

The transmitting fibers 10 transfer the infrared radiation from the radiation source 4 to the patient skin 6. When the patient skin 6 is in contact with the common plane of the transmitting fibers 10 and receiving fibers 16 at the contact section 14, the radiation from the transmitting fibers 10 is directly coupled into the patient skin 6 with no possibility of reflection from the skin's surface into any of the receiving fibers 16. Power is therefore forced to be diffused through the patient skin 6, where it is absorbed in a spectrally selective manner, before it returns through the patient skin 6 and into the receiving fibers 16. This selective absorption varies with the glucose level of the patient. Thus, the spectral pattern of the received power contains the information needed to make the glucose level measurement, which is the overall goal of the monitor with which the probe 2 of the present invention is used.

The isolation between the transmitting fibers 10 and the receiving fibers 16 is an important feature of this invention, since the isolation significantly improves the received spectral information's signal-to-background ratio, thereby permitting the subtle glucose information to be readily extracted. Similarly, surrounding each receiving fiber 16 by the chosen number of transmitting fibers 10 at the patient skin 6 optimizes the glucose absorption information content in the received signal, by providing a statistically appropriate average penetration path of optical power within the patient skin 6.

The receiving fibers 16 transfer the information-carrying infrared energy to the spectrograph 8, where it is optically dispersed for analysis. At the spectrograph 8, the receiving fibers 16 are arranged in a pattern compatible with the size and shape of each picture element or pixel at the output of the spectrograph 8. In one embodiment of a spectrograph 8, the pattern of the output pixels is linear, with matching rectangular sensor pixels. For example, the spectrograph 8 can be designed so that a grating therein disperses a collimated beam from a source mirror into a multiplicity of wavelengths, each diffracted in a slightly different direction. This process forms multiple overlapping collimated beams, each corresponding to a specific wavelength and direction, all of which are aimed substantially at a camera mirror in the spectrograph 8. The camera mirror focuses each of the various wavelengths at a slightly different location, forming an extended continuum of overlapping source array images at the detector array location.

One embodiment of a spectrograph 8 operates at substantially unity magnification, so that the size and shape of each source image are nominally identical to those of the source array. The detector array in the spectrograph 8 is oriented with its successive pixels aligned with the image continuum such that: each pixel captures a different wavelength region of the continuum, and the size of the detector pixels and the source are designed to be nearly identical, but with a small deliberate overlap. Furthermore, to optimize capture efficiency in the design of the spectrograph 8, the detector array plane can be tilted with respect to the central ray so that the astigmatic images formed by the camera mirror are elongated in the longer direction of each pixel at and near both ends of the array. This approach optimizes the concentration of the focused power on each pixel for each associated wavelength and extends the useful angular optical field well beyond that ordinarily associated with reflective optics.

Figure 4:
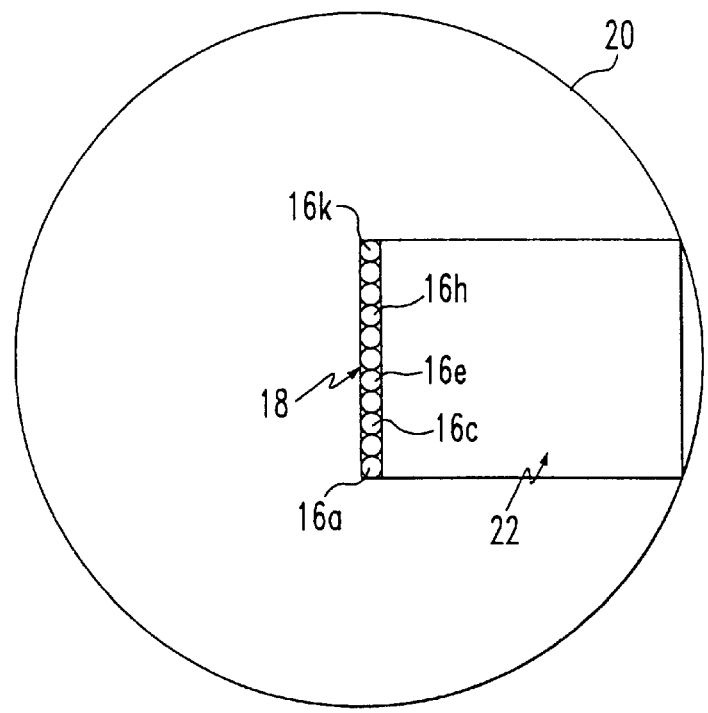
FIG. 4 is an end view of the receiving fibers where they enter the spectrograph.

In a preferred embodiment, the spectrograph detector is a multi-element photodetector array, each element of which is about ten times longer than it is wide. The receiving fibers 16, each having a core diameter substantially equal to the width of each array element, can be arranged in a straight line as shown in FIG. 4. Eleven receiving fibers 16a through 16k have been chosen in the preferred embodiment herein to ensure that the unity-magnification spectrograph image of the source array overfills the sensor pixels. The overfilling of these pixels provides an alignment margin and ensures that vibration effects do not result in error-producing variations in pixel signal during operation. The receiving fibers 16 can be held against an alignment surface 18 in a housing 20 by a keeper 22 or the like. Ideally, the receiving fibers 16 at the spectrograph termination are joined together by epoxy 24 or the like so that their precise alignment remains unchanged during operation. The numerical aperture of the receiving fibers 16 and the optics of the spectrograph 8 must be compatible, and the receiving fibers 16 and transmitting fibers 10 must be transmissive throughout the spectral region of operation. In some embodiments, these requirements necessitate transmission at wavelengths near or beyond $2\mu$. In such cases, fibers made substantially of fused silica are preferred. Low-OH$^-$ fiber is also preferred because absorption by that radical may be confused with glucose absorption in certain spectral regions, notably within the desired near-infrared range, and particularly in view of the inherently low level of glucose signals compared to the general level of skin signals.

In the preferred embodiment, hard-clad, low-OH$^-$ optical fiber of approximately 0.39 numerical aperture (n.a.) and 0.230 mm diameter (0.200 mm core) is used as the transmitting fibers 10 and the receiving fibers 16. The numerical aperture of the fiber is deliberately chosen to be larger than that of the spectrograph 8 (~0.3 n.a.) to ensure that the optics and grating are overfilled, even in the presence of operational vibration and thermal effects. One such fiber is 3M's FT-200-LMT, but other similar low-OH$^-$ fibers and other combinations of diameter and n.a. compatible with spectrographs or sensors of the preferred embodiment or other types are included within the scope and spirit of this invention.

In order to reduce the effects of vibration and thermal changes, the receiving fibers 16 are, in a preferred embodiment, enclosed in an insulating material type of structure. This is shown in more detail in FIG. 5. Although encasing the receiving fibers 16 in insulating material would appear to be straightforward, an approach which merely provides a thick insulating material wrapping around the receiving fibers 16 will tend to make the overall structure less flexible. In the present invention, this problem is overcome by two unique methods. The first method is to enclose the receiving fibers 16 in a small insulating tube that fits rather loosely inside of a larger insulating tube. The second method is to fix one end of the larger insulating tube while letting the other end float. These two methods yield a more flexible assembly and also greatly reduce the strain on the receiving fibers 16 when flexed.

Figure 5:
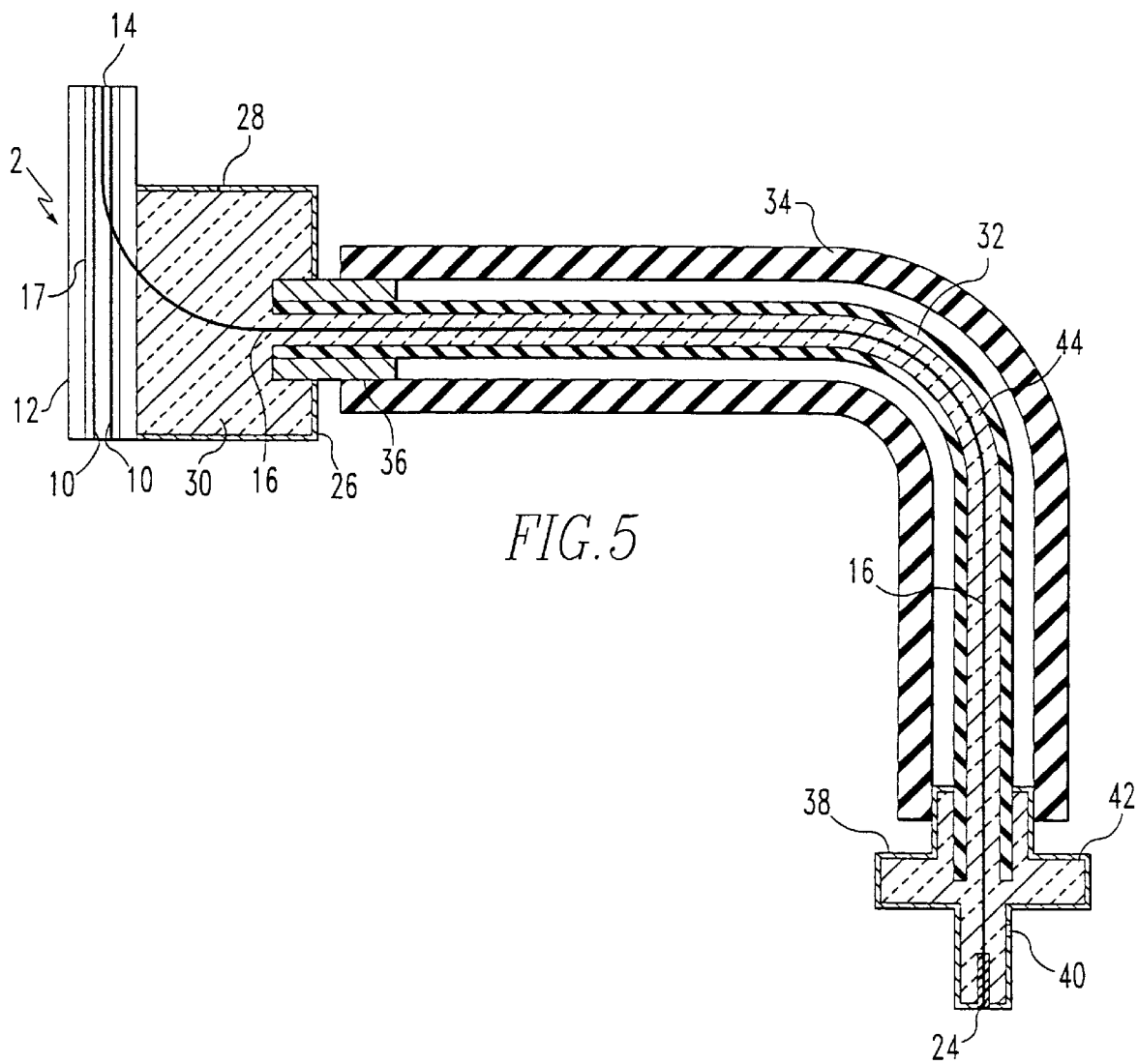
FIG. 5 is a schematic view showing one embodiment of an arrangement for protecting the receiving fibers between the patient contact and the spectrograph.

FIG. 5 shows a preferred embodiment of a structure for protecting the receiving fibers 16 in accordance with the present invention. As discussed above, the transmitting fibers 10 and the receiving fibers 16 are embedded in epoxy 17 or the like at the contact section 14 where it comes in contact with the patient. When the receiving fibers 16 leave the probe body 12, they pass into a first enclosure 26, which is preferably a box-like structure attached to the probe body 12 and filled, such as through hole 28, with insulating material 30 or the like. This is a particularly critical area because it forms the transition between the probe body 12 and the nested insulating tubes discussed above. When the receiving fibers 16 leave the first enclosure, they pass along the remainder of their length to the spectrograph 8 within a second enclosure formed from a first or inner insulating tube 32 immediately surrounding the receiving fibers 16 and a second or outer insulating tube 34 which surrounds and is spaced from the inner insulating tube 32. A slip ring 36 is affixed to one end of the inner tube 32 adjacent the first enclosure 26 and the slip ring 36 is securely affixed to the first enclosure 26. The other end of the inner tube 32 is attached to a receiving fiber housing 38 which provides the connection of the receiving fibers 16 encased in epoxy 24 to the spectrograph 8. The outer tube 34 is also securely affixed at one end to the receiving fiber housing 38 and its other end is slip fit onto the slip ring 36 adjacent the first enclosure 26. This arrangement provides flexibility between the outer tube 34 and its connections so that flexing of the inner tube 32 and outer tube 34 does not damage or stress the receiving fibers 16. The slip fit arrangement discussed above with slip ring 36 could be provided at the receiving fiber housing 38 adjacent the spectrograph 8, although the arrangement shown in FIG. 5 is believed to be preferred. It is preferred that the receiving fiber housing 38 be filled, such as through hole 40, with an insulating material 42 and that the interior of the inner tube 32 be filled with an insulating material. The first enclosure 26, the interior of the inner tube 32 and the receiving fiber housing 38 can be filled simultaneously with the same material through hole 28 or, preferably, through hole 40, since these elements are all interconnected in their interiors.

In a preferred embodiment, the receiving fibers 16 are surrounded by the inner tube 32 which is an insulating multi-layer sheath that encapsulates the receiving fibers 16. The receiving fibers 16 are loosely enclosed over their full length inside the lumen of a typically medium durometer elastomeric inner tube that exhibits adequate insulating properties. For optimal thermal and mechanical isolation, the receiving fibers 16 inside the lumen of the inner tube 32 may then be further protected by backfilling the inner tube 32 with a low durometer, insulating elastomeric potting compound 44. This material, inserted in a fluid state and then cured, surrounds the receiving fibers 16 directly and provides both additional thermal isolation and mechanical vibrational dampening to reduce microbending effects. Over the inner tube 32 in which the receiving fibers 16 are potted is an outer tube 34 of adequate :insulating properties which provides additional thermal and mechanical isolation. The outer tube 34 may be a typically medium durometer elastomeric tube or may be a more rigid tube. Multiple layers of various insulating materials may also be used to achieve the same effects as described above.

The foregoing discussion and the attached drawings are illustrative and non-limiting. They are descriptive of preferred means of realizing the invention for a fiber probe in a specific glucose sensor instrument design. Alternate implementations and variations evident to those skilled in the art, including other fiber array patterns, probe profiles, choices of materials, tube rigidity, insulating properties, backfilling, number of insulating layers, the use of an optical coupling interfaced to the spectrograph and the like, are also included within the scope and spirit of this invention. The invention is fully defined by the claims which follow.

We claim:

1. A probe suitable for use in the non-invasive sensing of glucose concentrations in the body of a patient, said probe comprising: at least three radiation receiving fibers extending between a probe body and a spectrograph, and spaced apart from each other in a substantially uniform manner and aligned in a predetermined fixed pattern at said probe body, a radiation transmitting means for conducting radiation from a radiation source and extending from the radiation source to the probe body, with said radiation transmitting means formed in said probe into ring means for conducting radiation in a ring-shaped area immediately surrounding each of said receiving fibers, with said radiation transmitting means and said receiving fibers terminating at said probe body in a unitary structure having an outer surface configured for contacting the skin of a patient, wherein the ring means passes radiation from said radiation source and into the patient in the areas immediately surrounding each receiving fiber and the receiving fibers detect said radiation passing back out of the patient and pass said detected radiation to the spectrograph.

2. The probe of claim 1 wherein said radiation transmitting means is formed of a plurality of radiation transmitting fibers and the ring means is formed from certain of said transmitting fibers immediately surrounding each receiving fiber in a ring-shaped pattern at the outer surface.

3. The probe of claim 2 wherein each receiving fiber is separated from its immediately adjacent receiving fiber by at least one transmitting fiber.

4. The probe of claim 2 wherein the transmitting fibers at the radiation source are arranged in an incoherent manner.

5. The probe of claim 4 wherein the transmitting fibers at the radiation source are arranged in a hexagonally packed circular pattern.

6. The probe of claim 2 wherein the transmitting fibers are arranged in a plurality of transmitting fiber rings surrounding each receiving fiber, with each ring arranged in a tightly packed hexagonal pattern from said transmitting fibers.

7. The probe of claim 6 wherein the transmitting fiber rings surrounding each receiving fiber share transmitting fibers with one or more transmitting fiber rings of receiving fibers immediately adjacent thereto.

8. The probe of claim 2 wherein the transmitting fibers are arranged in three transmitting fiber rings surrounding each receiving fiber, with each ring arranged in a tightly packed hexagonal pattern from said transmitting fibers.

9. The probe of claim 2 wherein the transmitting fibers and receiving fibers in said probe at said outer surface are affixed together with adhesive.

10. The probe of claim 1 wherein the receiving fibers are arranged in contact with each other and along a straight line at their end opposite the probe body and adjacent the spectrograph.

11. The probe of claim 1 wherein the receiving fibers are covered by an enclosure in the area between an outer portion of the probe body and their termination at the spectrograph.

12. The probe of claim 11 wherein the enclosure includes a first insulating enclosure immediately adjacent the probe body and a second insulating enclosure extending along the remaining length of the receiving fibers.

13. The probe of claim 12 wherein the first insulating enclosure is a hollow structure filled with an insulating material.

14. The probe of claim 12 wherein the second enclosure includes a first insulating tube immediately surrounding the receiving fibers and a second insulating tube spaced from and surrounding the first insulating tube.

15. The probe of claim 14 wherein one end of the second insulating tube is securely attached to the first insulating tube, while the other end of the second insulating tube is loosely attached to the first insulating tube and is moveable with respect thereto.

16. The probe of claim 15 wherein the end of the first insulating tube adjacent the probe body is attached to a slip ring which is attached to the first enclosure and the end of the second insulating tube adjacent the probe body is slip fit onto the slip ring.

17. The probe of claim 16 wherein the ends of the receiving fibers opposite the probe body are securely attached to a receiving fiber housing and the first insulating tube and second insulating tube are each securely attached to the receiving fiber housing.

18. The probe of claim 17 wherein the receiving fiber housing is a hollow structure filled with an insulating material.

19. The probe of claim 14 wherein an interior of the first insulating tube is filled with an elastomeric compound.

20. The probe of claim 1 wherein the radiation receiving fibers are aligned in a substantially straight line.

* * * * *

UNITED STATES PATENT AND TRADEMARK OFFICE
CERTIFICATE OF CORRECTION

PATENT NO. : 6,219,565 B1
DATED : April 17, 2001
INVENTOR(S) : James Cupp et al.

It is certified that error appears in the above-identified patent and that said Letters Patent is hereby corrected as shown below:

<u>Column 4,</u>
Line 63, "such that: each" should read -- such that each --.

<u>Column 5,</u>
Line 28, "beyond 2µ." should read -- beyond 2µm.--

<u>Column 6,</u>
Line 54, before "insulating" delete colon (:).

Signed and Sealed this

Thirtieth Day of October, 2001

Attest:

NICHOLAS P. GODICI
*Attesting Officer*   *Acting Director of the United States Patent and Trademark Office*